United States Patent
Pisani

(10) Patent No.: US 9,693,678 B2
(45) Date of Patent: Jul. 4, 2017

(54) NETWORK OF DEVICES FOR PERFORMING OPTICAL/OPTOMETRIC/OPTHALMOLOGICAL TESTS, AND METHOD FOR CONTROLLING SAID NETWORK OF DEVICES

(71) Applicant: REALVISION S.R.L., Milan (IT)

(72) Inventor: Sabino Pisani, Rescaldina (IT)

(73) Assignee: REALVISION S.R.L. (IT)

( * ) Notice: Subject to any disclaimer, the term of this patent is extended or adjusted under 35 U.S.C. 154(b) by 141 days.

(21) Appl. No.: 14/654,988

(22) PCT Filed: Oct. 22, 2012

(86) PCT No.: PCT/IT2012/000320
§ 371 (c)(1),
(2) Date: Jun. 23, 2015

(87) PCT Pub. No.: WO2014/064719
PCT Pub. Date: May 1, 2014

(65) Prior Publication Data
US 2015/0335235 A1    Nov. 26, 2015

(51) Int. Cl.
*A61B 3/10*    (2006.01)
*A61B 3/00*    (2006.01)
*A61B 3/08*    (2006.01)

(52) U.S. Cl.
CPC .......... *A61B 3/0058* (2013.01); *A61B 3/0025* (2013.01); *A61B 3/08* (2013.01)

(58) Field of Classification Search
CPC ......... A61B 3/102; A61B 3/0041; A61B 3/08; A61B 8/4472
USPC ................................. 351/205, 200, 246, 206
See application file for complete search history.

(56) References Cited

U.S. PATENT DOCUMENTS

| | | | |
|---|---|---|---|
| 2011/0085138 A1* | 4/2011 | Filar | A61B 3/12 351/206 |
| 2011/0157550 A1 | 6/2011 | Chen et al. | |
| 2012/0105609 A1 | 5/2012 | Qi | |

* cited by examiner

*Primary Examiner* — Hung Dang
(74) *Attorney, Agent, or Firm* — Banner & Witcoff, Ltd.

(57) ABSTRACT

A network of devices for performing optical/optometric/ophthalmological tests comprises at least one patient-interface designed to display three-dimensional and/or stereoscopic images and provided with at least one display screen with a nested, three-dimensional projection/display capability, and at least one operator-interface designed to apply control and management functions to the patient-interface.

17 Claims, 1 Drawing Sheet

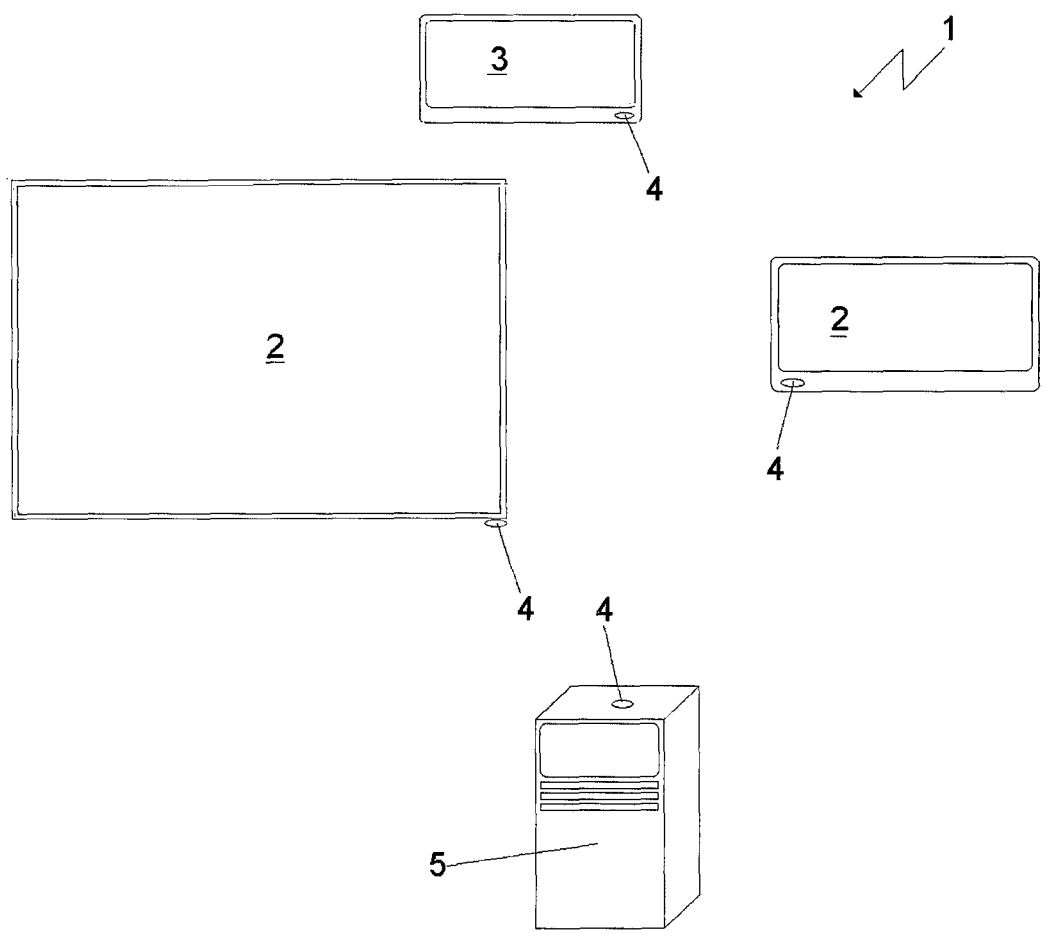

NETWORK OF DEVICES FOR PERFORMING OPTICAL/OPTOMETRIC/OPTHALMOLOGICAL TESTS, AND METHOD FOR CONTROLLING SAID NETWORK OF DEVICES

TECHNICAL FIELD

This invention relates to a network of devices for performing optical/optometric/ophthalmological tests intended to measure the visual abilities (and to detect possible physiopathological disorders) of patients. The invention also relates to a method for controlling such a network of devices.

BACKGROUND ART

As is known, the activities of opticians and ophthalmologists typically include assessing the abilities (or inabilities) of a patient's visual system. This is done by inducing specific movements and neurological responses in the patient's eye (and hence in the optic nerve and/or muscles which control eye movements): such stimuli are created by showing the patient target figures of different kinds, which may be static (in time) or dynamically variable.

In particular, some vision tests involve stimulating the patient's eyes through target images which appear three-dimensional: indeed, the purpose of such tests is to induce the neurovisual mechanism of what is known as "stereoscopic vision", thanks to which the patient's brain processes and perceives a three-dimensional view of a target object which is in fact represented in two dimensions (but with appropriate graphical tricks) on a physical medium: to induce stereoscopic vision, therefore, the patient is made to wear stereoscopic glasses, which stimulate this type of vision.

The test methods (and hence the apparatuses and physical media of the target images) used nowadays have some disadvantages, however: the main disadvantage is the need—just mentioned—to make the patient wear stereoscopic glasses, which often cause discomfort and an unpleasant sensation in particularly susceptible people.

Further, the need to use stereoscopic glasses, which by their very nature must be placed in direct contact with patients, gives rise to considerable complications in terms of operating flexibility (and thus management costs) on account of the need to have glasses of different "sizes" adaptable to different facial features or to clean/disinfect the glasses after each use.

Moreover, it should also be stressed that the data relating to the results of the optical/ophthalmological tests, as performed in current practice, are collected on physical media (typically paper) separate from the devices used to perform the tests: this has considerable logistic disadvantages and increases the workload of the operator/optician who must coordinate the actions involved in the performance of the actual test with the actions required for annotating and classifying the test results (thus increasing the risk of error and creating undesirable work stress, as well as unduly lengthening the total amount of time needed for the test, to the detriment of the patient's conditions).

DISCLOSURE OF THE INVENTION

This invention therefore has for its purpose to provide a network of devices for performing optical/ophthalmological tests which overcomes the above mentioned disadvantages and which allows implementing a control method that is more rapid (quicker to run), more accurate (in collecting test results) and less onerous both for the operator/optician and for the patient.

The main aim of the invention is to provide a network of devices which can guarantee quick and easy implementing of any number and range of optical/ophthalmological tests, without therefore necessitating the purchase of specific physical media for additional tests or tests which are not currently available.

Another aim of the invention is to provide a method for controlling a network of devices, preferably electronic, which allows a very high degree of functional and operational integration in order to alleviate the burden on the operator (and on the patient!) and also to adapt to different logistic situations at different test locations, such as opticians' shops, doctors' surgeries, and the like.

The technical purpose and aims specified are substantially achieved by a network of devices, preferably electronic and/or multimedia devices, and by a method for controlling such a network of devices, having the features described in one or more of the appended claims.

BRIEF DESCRIPTION OF DRAWINGS

A preferred, non-limiting embodiment of a network of devices according to the invention will now be described by way of an example with reference to the accompanying drawing, where:

FIG. 1 is schematic representation of a network of devices for performing optical/optometric/ophthalmological tests according to the invention.

DETAILED DESCRIPTION OF THE PREFERRED EMBODIMENTS OF THE INVENTION

With reference to the accompanying drawing, the network of devices is denoted in its entirety by the reference numeral 1 and substantially comprises at least one patient-interface 2 (described in more detail below) and at least one operator-interface 3 designed to apply control and management functions to the patient-interface 2.

Advantageously, at least one patient-interface 2 (and depending on specific requirements, the operator-interface 3, too) can display three-dimensional and/or stereoscopic images and includes at least one display screen with a nested, three-dimensional projection/display capability: In other words, the patient-interface 2 and/or the operator-interface 3 can generate, on a specific display device, images which are immediately perceptible as three-dimensional, without necessitating glasses (whether "active" or "passive") which induce the effect of stereoscopic vision.

It should therefore be noted that according to this invention the interfaces 2 and/or 3 are designed to display three-dimensional and/or stereoscopic images: for this purpose, they are provided with at least one screen with a "nested" three-dimensional projection/display capability. The latter expression is used to mean the ability to generate/process and show on the screen a three-dimensional image which can be viewed/perceived without the aid of specific glasses.

Looking in more detail at the structure of the invention, it may also be noted that the patient-interface 2 and/or the operator-interface 3 comprise an electronic/multimedia device which may comprise the following main parts:

a data processing hardware comprising at least one screen or display whose optical resolution must be high enough to allow nested three-dimensional images to be generated/displayed which are clear enough to allow the optical/optometric tests to be performed;

a control software which is nestable in the data processing hardware (and which controls at least the main screen or display functions); and communication means 4 which are designed to functionally interconnect the patient-interface 2 with the operator-interface 3 (and which from a functional viewpoint are operatively connected at least to the data processing hardware).

Typically, to provide improved handiness and portability for both the operator and the patient, the electronic/multimedia devices may be of the type known nowadays as "tablets" or the like (although, depending on specific requirements, they may also be suitable fixed or mobile computer monitors/television screens).

As regards the performance of these devices and bearing in mind also what has just been said as to the images having to be "clear enough" at least for viewing by the patient, the screen or display of the interface 2 and/or 3 should possess the following combination of operating parameters:

a minimum resolution of between 1280×790 pixels (for example, 1280×800 pixels) and 1920×1080 pixels; and a diagonal screen size of between 8.1 inches and 55 inches.

With reference to "diagonal screen size", it should be noted that this invention allows implementing an extremely wide range of device networks as a function not only of the patient's needs but also of the logistic situation in which the optical/optometric/ophthalmological tests are performed.

For example, if the space available is confined or if the patient wants or has to be in a condition to view the images from a distance which may be referred to as "near" (as described in detail below), it is possible to use tablets with one of the following screens or displays:

8.1 inch screen with resolution of at least 1280×790 pixels or 1280×800 pixels (to be used preferably as patient-interface 2); and/or 9.7 inch screen with resolution of at least 1280×790 pixels or 1280×800 pixels (to be used preferably as operator-interface 3).

On the other hand, if more working space is available, giving the patient the possibility of viewing the screen or display from a greater distance, the following TV screens or computer monitors can be used:

21 inch screen with resolution of at least 1920×1080 pixels; and/or 23 inch screen with resolution of at least 1920×1080 pixels; and/or 34 inch screen with resolution of at least 1920×1080 pixels; and/or 55 inch screen with resolution of at least 1920×1080 pixels.

To implement and maintain the communication between the interfaces of this network, communication means 4, comprising units for transmitting and/or receiving signals in wireless mode, are conveniently provided: looking in more detail at the physical structure of the network of devices, the transmission and/or receiving units are circuitally connected to the respective data processing hardware of the patient-interface 2 and/or of the operator-interface 3 (and for example can be implemented by respective "dongles" with receiving and transmitting functions and based on a suitable programming language, such as the well-known "android").

In order to guarantee high data storage capacity (whether the data is that relating to the optical/optometric/ophthalmological tests or to the results of tests on one or more patients), the network 1 can be further expanded with a remote memory device 5 (which may conveniently be a "server" type processing machine): the remote memory device 5 is connected to the patient-interface 2 and/or to the operator-interface 3 (typically by way of suitable communication means 4 which, as just mentioned, may be of a wireless type) and is designed to store in, unload from or load into the interfaces 2 and/or 3 the control software and/or a predetermined number of fixed or dynamic target images usable at least in the patient-interface 2 perform optical/optometric/ophthalmological tests.

The possibility of storing the target images (or, if necessary, other types of data or control software instructions) in the remote device 5 allows the overall costs of the hardware to be limited: indeed, only data and instructions suitably pre-selected by the operator are sent, at the time of effective use, to the patient-interfaces 2, which may therefore have relatively inexpensive storage hardware requirements.

This invention also has for an object a novel and original method for controlling and managing a network of devices as described up to here (and as claimed below): the method basically comprises a step of sending a predetermined sequence of target images from an operator-interface 3 (or, depending on the type of network of devices used, from the remote memory device 5) to at least one patient-interface 2, and a step of displaying that predetermined sequence of target images on the screen or display of the patient-interface 2.

Advantageously, the step of displaying the sequence of target images (which might also be a single image, whether fixed or dynamically variable over time) comprises a sub-step of generating/processing/displaying the target image in stereoscopic and/or three-dimensional mode: this sub-step is physically implemented in a screen or display with "nested", three-dimensional and/or stereoscopic capabilities . . . and that is, without the person looking at the screen or display having to wear stereoscopic glasses.

The method of the invention also offers the possibility of managing operating parameters of the sequence of target images in such a way as to be able to adapt to the needs of both the operator and the patient.

The operating parameters this operating step may be applied to are at least the following:

a length of time one or more target images remain displayed on the screen or display of the patient-interface 2;

a stereoscopic breakdown of a two-dimensional image and its conversion, preferably reversible, and displaying as a three-dimensional image on the screen or display of the patient-interface 2 (and, as just mentioned, also the "reverse" conversion from a three-dimensional and/or stereoscopic format to a two-dimensional format); and a frame rate and/or a speed of driving and/or changing the colour (brightness, contrast, colour saturation and so on) or geometry (enlargement factor, geometric distortion, apparent curvature of the visual plane and so on) of at least one target image, whether fixed or dynamically variable over time.

Operatively, the sub-step of managing the operating parameters may be remotely controlled through the operator-interface 3 and/or through the remote memory device 5, if the latter device is provided with means which allow an operator to enter commands.

Again in terms of offering a possibility of choice to the operator (who is usually the person in charge of performing the test on the patient and of assessing the results of the tests), it is possible to pre-select a predetermined sequence of target images, preferably from the operator-interface 3: such pre-selection is done by extracting one or more subsets of target images (and the subset may be sorted according to any time sequence) from the entire contents of the memory of the operator-interface 3 or of the remote device 5, and can be conveniently associated with a sub-step of defining a selection index correlated with the pre-selected sequence of target images.

In terms of user-friendliness, defining the selection index just mentioned can be done with the aid of a suitable mode of displaying the selfsame selection index on the screen or display of the operator-interface 3: for example, the control method might be capable of dividing the screen or display of the operator-interface 3 into two areas of any shape, the first area containing the entire database of target images and the second area containing the subset chosen to form the pre-selected sequence: the operator can select one or more target images contained in the first area using a suitable command (for example a touch command) and move/drag/copy them into the second area, and once the pre-selection has been completed, the operator can access a command for sending the pre-selected images to the patient-interface 2.

While the optical/optometric/ophthalmological tests are being performed (based on the sequence of target images chosen by the operator and shown to the patient), it is also possible to enter, and preferably save, test parameters correlated with the neuro-optical reactions of the patient (or rather, of the patient associated with the patient-interface 2): this control step may be performed on the operator-interface 3 or on the remote memory device 5, for example by way of a suitable "dialogue box" editable by the operator.

Also to guarantee a high level of interactivity for the network of devices, the network control method may also comprise a step of sending feedback from the patient-interface 2 to the operator-interface 3: conveniently, the feedback may comprise a predetermined set of qualitative and/or quantitative response parameters chosen by the patient in response to a neuro-optical stimulus produced by at least one target image and/or by the predetermined sequence of target images.

In one possible embodiment of the feedback step just mentioned, the patient might have at his/her disposal a specific frame on the screen or display of his/her interface 2 (which in turn might have a touch-screen capability) showing predetermined responses selectable by the patient as a function of the visual stimulus he/she has received, or a free text box in which to write or type a response correlated with the visual stimulus received.

Once the response has been filled in or selected from the specific frame, the feedback it constitutes can be sent to the operator-interface 3 and/or to the remote memory device 5 automatically or by a specific patient command.

Conveniently, in order to harmonize the operation of the network of devices 1 according to the invention, the control method might also comprise other steps of synchronizing the communications between the interfaces 2 and 3 (and, if present, the device 5). This communication synchronization occurs through the communication means 4 and may comprise several operating sub-steps, including, for example:
recognizing, either automatically or upon operator input, other patient-interfaces 2 which can be entered in the network 1 at later stages;
disconnecting one or more patient-interfaces 2, either automatically or on condition (for example after a certain period of inactivity);
switching the communication means 4 on and/or off and driving them synchronously or sequentially in the case where one operator-interface 3 has to control two or more patient-interfaces 2.

With reference in particular to the synchronization function just mentioned, the method of the invention might comprise a step of simultaneously controlling/driving two different types of patient-interfaces which may be, for example, an interface for near use and an interface for distance use: the patient-interface for near use might be, for example, a tablet which can be positioned at a viewing distance (from the patient) of between 20 and 100 cm, preferably between 25 and 40 cm, whilst the patient-interface for distance use might be, for example, a computer monitor or a television screen which can be positioned at a viewing distance (from the patient) of between 200 and 800 cm, preferably between 300 and 600 cm.

According to another feature of this method, it is also possible to implement a step of tracking and saving a patient's eye activity: such eye activity may be expressed at least in terms of focussing point path of at least one eye on the screen or display of the patient-interface 2 and is implemented, at hardware level, through a suitable image capturing and identification tool (for example, a camera or an optical device) visually facing the patient, and hence nested in the patient-interface 2.

If the control method has to be applied to a network comprising (simultaneously) a patient-interface 2 for near use and a patient-interface for distance use, the screen of the operator-interface may be divided into areas corresponding to the three interfaces making up the network itself: in each of these areas, it is therefore possible to send/load suitable pre-selected sequences of target images which, for the two patient-interfaces may in turn be identical or different, so that different eye tests can be performed according to the patient's viewing distance.

As regards the available range of optical/optometric/ophthalmological tests, this method (and the network of devices based on it) may have any contents whatsoever in terms of quality and quantity: more specifically, the target images, whether fixed or dynamically variable over time, may be stored in the remote memory device 5 and may be downloaded, for example through a system of electronic transactions, to the operator-interface 3. While the tests are being performed on patients, the operator-interfaces 3 may in turn send target images to the patient-interfaces served by them.

To guarantee the maximum compatibility between the hardware devices making up the network, the programming language and/or operating system loaded into the devices is advantageously a single one, common to all of the devices (for example, android type software). Also, to minimize structural complexity in terms of interaction with operators and/or patients, the interfaces 2 and/or 3, as well as the device 5, may be equipped with screens or displays capable of receiving touch commands.

As regards the range of tests which may be performed, it may be noted that these include tests of known type (based on fixed or dynamically variable images) or also tests of an innovative nature: generally speaking, this invention is therefore able to implement and carry out the following types of tests (as they are known in the jargon of the trade):
"Snellen" optotype;
"Sloan" optotype;

"Numbers" optotype;
"Albini E" optotype;
"Landolt C" optotype;
"Kolt" optotype;
"Square wave/sinusoidal bars" optotype;
"HOTV" optotype;
"Binocular ETDRS", "Right ETDRS" and "left ETDRS" optotypes;
circular optotypes with visual acuity from 0.10 a 2.0 tenths;
optotype with stereoscopic letters;
optotypes for monocular vision in a binocular field;
quadrants for assessment of astigmatism: "A grid" (version for adults and/or version for children);
quadrants for assessment of astigmatism: "Clock" (versions "A" and/or "B");
quadrants for assessment of astigmatism: "dots in circle" and/or "dots in hexagon";
"Quadrant" test;
"Polarized ray" test;
"Rodenstock" test for near-sighted astigmatism;
"1" and/or "2" and/or "3" balancing test, with visual acuity from 0.50 to 0.80;
red/green balancing test, with visual acuity from 0.4 to 0.6;
"Osterberg" test;
"Cowen C" test (circles and/or dots);
fixation aimings: horizontal aiming with acuity from 0.80 to 1.00 tenths;
fixation aimings: horizontal aiming with acuity of 0.8 tenths;
fixation point (daytime or night-time aiming)
Amsler grid;
assessment of sense of colour;
Schober test;
Mallet test (horizontal OXO and/or vertical OXO);
Osterberg stereo test;
horizontal and/or vertical phoria test;
"Worth lights" fusion test;
"Random dot" fusion test;
target images for retinoscopy: "mountain landscape" and/or "lakeside view";
MKH method: K cross test;
MKH method: ZV vertical indicator;
MKH method: ZO horizontal Indicator;
MKH method: DZ double indicator;
MKH method: H vertical coincidence test;
horizontal coincidence test;
"ST stereo triangles" test, including sub-test for fixation disparities varying from 6'; 9'; 12' of arc;
"V stereo balancing" test, including sub-test for fixation disparities varying from 6'; 9'; 12' of arc;
"D6/D8 stereo circles" test, with stereo-acuity from 5' to 30" of arc;
"D6/D8 stereo lines" test, with stereo-acuity from 5' to 10" of arc;
contrast sensitivity test, with Gabor images and with acuity from 0.75 to 18 cycles per degree;
"Contrast Sensitivity Chart" test (on 6 lines and with visual acuity from 0.30 to 1.95 tenths);
"CSC 12 lines" test;
PSRT glare recovery test;
dusk/dawn vision test;
glare sensitivity test;
"preferential looking" test;
"dynamic visual acuity" test;
"haploscopic aiming" fixation disparity test;
static and/or dynamic vectographic images;
images randomly presented at central/peripheral positions;
static and/or dynamic targets for eye motility, visual attention, visual memory and coordination;
vectographic aimings;
vision-posture interaction test, by means of blood pressure check footboards;
visual-auditory integration test;
static and/or dynamic test for assessment of foveal alignment;
tests based on anti-suppressive tables and/or on amblyopic stimulation tables;
tests based on vision rehabilitation tables; and
tests based on reading pieces of text with stereoscopic phonemes, with or without auditory stimulation.

The invention achieves numerous advantages.

Indeed, thanks to the particular make-up of the network of devices and the particular capabilities of displaying three-dimensional images without using stereoscopic glasses, it is possible to improve significantly the quality of the tests performed on the patient, who is not only completely free of the neuro-physiological stress that comes from the use of glasses but who is also placed more at ease ergonomically and psychologically.

At the same time, the "open" structure of the network of devices and hence the possibility of expanding or reducing it (in terms of number of interconnected devices) or to add/remove test-related material makes this invention ideal for medical operators/opticians work structures at any operating level, offering a full range of operational capabilities at a proportionate cost which can be "scaled" with great precision according to the logistic context in which the tests may need to be performed.

The special control process (which as described above may regard not only transmission and management of the target images but also receiving and storing the feedback produced by the patient in response to the target images) implemented by the method of the invention allows the operator to take extremely quick and precise action on any visual parameter, thus obtaining better and more controllable responses from the patient.

Further, in all the possible embodiments of the network of devices according to the invention, (and, more specifically, by increasing the number of patient-interfaces served by one or more operator-interfaces), it is possible to integrate additional functional means both at a physical/hardware level and "virtual" functional or software level, thus making the network of devices extremely flexible and adaptable, by allowing it to be expanded (or made more simple) in terms of total number of interconnected devices in the network.

Moreover, the ease with which the interfaces associable with the network can be controlled, and the high capability of transferring information and control instructions/signals make for high operating dependability and hence economy of use, with extremely advantageous amortization times and a significant improvement in the cost/benefit ratio compared with the methods and (mainly "analog") physical devices known in the prior art.

The invention claimed is:

1. A network of devices for performing optical/optometric/ophthalmological tests on at least one patient, comprising:
    at least one patient-interface;
    at least one operator-interface designed to apply control and management functions to the at least one patient-interface; and the at least one patient interface comprising a tablet configured to display at least one of a three dimensional image and a stereoscopic image and provided with a display screen with a nested, three-dimensional projection, display capability.

2. The network according to claim 1, further comprising a patient interface for distance view, selected from the group consisting of a TV screen and computer monitor, wherein the patient interface has a diagonal size between 21 inches and 55 inches and a resolution of at least 1920×1080 pixels.

3. The network according to claim 1, wherein at least one of the patient-interface and the operator-interface comprises a device having:
 a data processing hardware comprising at least one screen or display capable of receiving touch commands and having a minimum resolution of between 120×790 pixels and 1920×1080 pixels and diagonal screen size of between 8.1 inches and 55 inches;
 a control software which is nestable in the data processing hardware; and
 communication means which is configured to interconnect the patient-interface with the operator-interface and which are operatively connected at least to the data processing hardware, these devices comprising a tablet or like type or being computer monitors/television screens.

4. The network according to claim 3, wherein the communication means comprises units for at least one of transmitting and receiving signals in a wireless mode, at least one of transmission and reception units being circuitally connected to the respective data processing hardware of at least one of the patient-interface and the operator-interface.

5. The network according to claim 1, further comprising a remote memory device connected to at least one of the patient-interface and the operator-interface and configured to store in, unload from or load into at least one of the interfaces, control software, and predetermined number of fixed or dynamic target images usable at least in the patient-interface to perform optical/ophthalmological tests.

6. A method for controlling and managing a network of devices comprising the steps of:
 sending a predetermined sequence of target images from at least one of a operator-interface and a from the remote memory device to at least one patient-interface; and
 displaying a predetermined sequence of target images on a screen or display of the at least one patient-interface, the displaying comprising displaying at least one target image in at least one of a stereoscopic mode and a three-dimensional mode on a tablet.

7. The method according to claim 6, further comprising a step of managing operating parameters of the selfsame sequence, the operating parameters comprising at least:
 a length of time one or more target images remain displayed on the screen or display of the patient-interface;
 a stereoscopic breakdown of a two-dimensional image and its conversion and displaying, reversibly, as a three-dimensional image on the screen or display of the patient-interface; and
 at least one of a frame rate, a speed of driving, changing the colour or geometry of at least one target image, whether fixed or dynamically variable over time, the sub-step of managing operating parameters being controlled remotely through one of the operator-interface and the remote memory device.

8. The method according to claim 6, further comprising a step of pre-selecting, from the operator-interface, a predetermined sequence of target images, and further comprising defining a selection index correlated with the predetermined sequence of target images pre-selected on the screen or display of the selfsame operator-interface.

9. The method according to claim 6, further comprising a step of entering test parameters correlated with the neuro-optical reactions of a patient associated with the patient-interface, this step being performed on the operator-interface or on the remote memory device.

10. The method according to claim 6, further comprising a step of sending feedback from the patient-interface to the operator-interface, the feedback comprising a predetermined set of qualitative and/or quantitative response parameters chosen by the patient in response to a neuro-optical stimulus produced by at least one of at least one target image and the predetermined sequence of target images and being obtained by filling in/choosing from a frame displayed on the patient-interface, a content of the frame being sent to at least one of the operator-interface and the remote memory device.

11. The method according to claim 6, further comprising synchronizing the communications between two of the patient-interface, the operator-interface and the remote memory device.

12. The method according to claim 11, wherein the step of synchronizing the communications comprises:
 recognizing, either automatically or upon operator input, other patient-interfaces which can be entered in the network of devices at later stages;
 disconnecting one or more patient-interfaces from the network of devices, either automatically or on condition, after a certain period of inactivity; and
 switching the communication means on or off.

13. The method according to claim 6, further comprising a step of synchronously or sequentially activating more than one patient-interface through the operator-interface.

14. The method according to claim 13, wherein the step of activating more than one patient-interface comprises simultaneously controlling/driving the tablet for near use and the patient interface for distance use, the step of driving more than one patient-interface being configured by dividing the screen of the operator-interface into areas corresponding to at least one of the patient interface and the operator interface making up the network of devices, it being possible to send to and possible to load into each of the divisions a respective preselected sequence of target images.

15. The method according to claim 14, wherein the patient-interface for near use is the tablet which can be positioned at a viewing distance from the patient of between 20 and 100 cm, the patient-interface for distance use being a computer monitor or a television screen which can be positioned at a viewing distance from the patient of between 200 and 800 cm.

16. The method according to claim 15, wherein the patient-interface for near use is the tablet which can be positioned at a viewing distance from the patient of between 25 and 40 cm, the patient-interface for distance use being the computer monitor or the television screen which can be positioned at a viewing distance from the patient of between 300 and 600 cm.

17. A method for performing optical/optometric/ophthalmological tests on at least one patient, comprising the steps of:
 sending a predetermined sequence of target images from at least one of a operator-interface and a remote memory device to at least one patient-interface; and displaying a predetermined sequence of target images on a screen or display of the at least one patient-interface, the displaying comprising displaying at least one target image in at least one of a stereoscopic mode and a three-dimensional mode on a tablet.

* * * * *